(12) United States Patent
Cha et al.

(10) Patent No.: US 7,073,513 B2
(45) Date of Patent: Jul. 11, 2006

(54) SUPERCONDUCTING MAGNETIC CONTROL SYSTEM FOR MANIPULATION OF PARTICULATE MATTER AND MAGNETIC PROBES IN MEDICAL AND INDUSTRIAL APPLICATIONS

(75) Inventors: Yung Sheng Cha, Darien, IL (US); John R. Hull, Downers Grove, IL (US); Thomas R. Askew, Kalamazoo, MI (US)

(73) Assignee: The University of Chicago, Chicago, IL (US)

( * ) Notice: Subject to any disclaimer, the term of this patent is extended or adjusted under 35 U.S.C. 154(b) by 615 days.

(21) Appl. No.: 10/445,681

(22) Filed: May 27, 2003

(65) Prior Publication Data
US 2004/0242429 A1 Dec. 2, 2004

(51) Int. Cl.
*A61B 19/00* (2006.01)
*H01H 47/00* (2006.01)

(52) U.S. Cl. .................. 128/899; 361/141; 361/143; 361/149

(58) Field of Classification Search ............... 128/899; 600/9; 361/141–146, 149; 505/100, 400
See application file for complete search history.

(56) References Cited

U.S. PATENT DOCUMENTS 5,654,864 A * 8/1997 Ritter et al. ............. 361/141
6,786,219 B1 * 9/2004 Garibaldi et al. .......... 128/899
6,842,324 B1 * 1/2005 Eyssa ....................... 361/141
2003/0231091 A1 * 12/2003 Tomita et al. ............. 335/302

OTHER PUBLICATIONS

Perry's Chemical Engineers' Handbook, McGraw-Hill Book Company, 6th edition, R.H. Perry and D.W.Green, Section 21, pp. 33-41 (1984).
D.C. Meeker, E.H. Maslen, R.C. Ritter and F.M. Creighton, Optimal Realization of Arbitrary Forces in a Magnetic Stereotaxis Systems, IEEE Trans. on Magnetics, vol. 32, No. 2, Mar. 1996, pp. 320-328.

* cited by examiner

Primary Examiner—John P. Lacyk
(74) Attorney, Agent, or Firm—Emrich & Dithmar LLC (57) ABSTRACT

A system and method of controlling movement of magnetic material with at least first and second high temperature superconductors at spaced locations. A plurality of solenoids are associated with the superconductors to induce a persistent currents in preselected high temperature superconductors establishing a plurality of magnetic fields in response to pulsed currents introduced to one or more of the solenoids. Control mechanism in communication with said solenoids and/or said high temperature superconductors are used to demagnetize selected ones of the high temperature superconductors to reduce the magnetic fields substantially to zero. Magnetic material is moved between magnetic fields by establishing the presence thereof and thereafter reducing magnetic fields substantially to zero and establishing magnetic fields in other superconductors arranged in a predetermined configuration.

25 Claims, 7 Drawing Sheets

SUPERCONDUCTING MAGNETIC CONTROL SYSTEM FOR MANIPULATION OF PARTICULATE MATTER AND MAGNETIC PROBES IN MEDICAL AND INDUSTRIAL APPLICATIONS

CONTRACTUAL ORIGIN OF THE INVENTION

The United States Government has rights in this invention pursuant to Contract No. W-31-109-ENG-38 between the U.S. Department of Energy (DOE) and The University of Chicago representing Argonne National Laboratory.

BACKGROUND OF THE INVENTION

Using magnetic particles as seeds for delivering drugs and therapy to targeted areas such as brain tumors and blood clots has been pursued for several decades. One area of research is to magnetically maneuver catheters through the vasculature for both diagnosis and delivery of therapy, and another is to magnetically manipulate small volumes of magnetic particles or powder after injection into the blood stream. This technique was to be used to induce thrombosis of intracranial aneurysms, and for the precise placement of ferromagnetic contrast agents for x-ray imaging. Other medical applications (such as urological, pulmonary, and orthopedic uses of the magnetic manipulation of magnetic particles and catheters) have been disclosed in the art.

Industrial applications of manipulating magnetic particles include magnetic separations and magnetic conveyer systems. The principle of magnetic control in either medical or industrial systems is to generate enough magnetic forces to move the magnetic parts or particles in the desired direction. Magnetic forces are proportional to the product of the magnetic field and its gradient. Therefore, generation and control of magnetic fields and its gradients are the main focus of a magnetic manipulation system. The magnetic particles or the tip of a catheter can be either soft magnetic (ferromagnetic) materials or hard ferromagnets such as NdFeB. For medical applications, the key issue is how to move the magnetic particles in a precise trajectory through human tissues, including blood vessels.

Currently, there are two methods of producing magnetic fields and field gradients for manipulating the magnetic particles in human tissue. The first method is to use permanent magnets and the second method is to use electromagnets (either conventional copper coil at room temperature or superconducting coil at liquid helium temperature). However, both methods have serious drawbacks in the amount of heat produced or in the size of the magnetic field produced by the magnets.

SUMMARY OF THE INVENTION

According, it is a principal object of the present invention to provide a method, system and apparatus of controlling magnetic material using high temperature superconductors.

Another object of the present invention is to provide a method, system and apparatus for controlling movement of magnetic material by introducing persistent currents in high temperature superconductors which can be reduced to zero in selected ones, thereby selectively creating and dissipating magnetic fields thereby moving magnetic material.

Another object of the invention is to provide trapped magnetic fields in a plurality of high temperature superconductors located at predetermined spaced locations.

Still another object of the present invention is to provide a method of controlling movement of magnetic material, comprising providing at least first and second high temperature superconductors at spaced locations, magnetizing at least one of the high temperature superconductors to establish a first magnetic field, magnetizing at least one other of the high temperature superconductors to establish a second magnetic field, and demagnetizing at least one of the high temperature superconductors to reduce the first magnetic field substantially to zero, whereby magnetic material near the first magnetic field will be attracted thereto during the presence thereof and when the first magnetic field is reduced substantially to zero the magnetic material will be attracted to the second magnetic field, thereby causing movement of magnetic material toward and away from the first and second magnetic fields.

A further object of the invention is to provide a method of controlling movement of magnetic material, comprising providing at least first and second high temperature superconductors at spaced locations, introducing a persistent current in at least one of the high temperature superconductors to establish a first magnetic field, introducing a persistent current in at least one other of the high temperature superconductors to establish a second magnetic field, and demagnetizing at least one of the high temperature superconductors to reduce the first magnetic field substantially to zero, whereby magnetic material near the first magnetic field will be attracted thereto during the presence thereof and when the first magnetic field is reduced substantially to zero then the magnetic material will be attracted to the second magnetic field, thereby causing movement of magnetic material toward and away from the first and second magnetic fields.

A final object of the invention is to provide a system of controlling movement of magnetic material, comprising at least first and second high temperature superconductors at spaced locations, a plurality of solenoids associated with the superconductors to induce persistent currents in preselected high temperature superconductors establishing a plurality of magnetic fields in response to pulsed currents introduced to one or more of the solenoids, and control mechanism in communication with the solenoids and/or the high temperature superconductors to demagnetize selected ones of the high temperature superconductors to reduce the magnetic fields substantially to zero, whereby magnetic material is moved between magnetic fields by establishing the presence thereof and thereafter reducing magnetic fields substantially to zero and establishing magnetic fields in other superconductors arranged in a predetermined configuration.

The invention consists of certain novel features and a combination of parts hereinafter fully described, illustrated in the accompanying drawings, and particularly pointed out in the appended claims, it being understood that various changes in the details may be made without departing from the spirit, or sacrificing any of the advantages of the present invention.

DETAILED DESCRIPTION OF THE PREFERRED EMBODIMENT

The inventive method and system employs pulsed-field solenoid coils with high-Tc superconductor inserts in the form of cylindrical disks or rings. Pulsed current is used to magnetize and de-magnetize the superconductor insert. The method and system utilizes the unique property of magnetic flux pinning and flux trapping in high-Tc superconductors. Furthermore, unlike the conventional methods and systems, the inventive system and method of generating magnetic field and magnetic field gradient is fully reversible by de-magnetizing the superconductor. Moreover, the combination of pulsed-field solenoids and high-Tc superconductor inserts provides additional capability and flexibility in propelling and controlling of the magnetic particles in human tissue beyond that achievable from either permanent magnets or electromagnets.

Using superconductor inserts to trap magnetic field is known in the art. Magnetic fields much larger than that produced by permanent magnets can be trapped in and around high-Tc superconductors. For example, magnetic flux density of 2 Tesla can be trapped in $SmBa_2Cu_3O_7$ disk (30–36 mm in diameter, and 15 mm in thickness) at 77 K. At 50 K, the trapped field increased to 6 Tesla. It has been reported that 4.6 Tesla can be trapped at 57.9 K in a $YBa_2Cu_3O_7$ (YBCO) disk with a diameter of 26 mm. Maximum trapped fields can be further increased by doping the superconductor with silver or by irradiation. Because trapped fields increase with decreasing temperature, even larger trapped fields can be achieved at still lower temperatures. As mentioned previously, this invention uses the combination of magnetizing (flux pinning and trapping) and de-magnetizing (de-pinning and untrapping) of high temperature superconductors to control the movement of the magnetic materials.

Figure 1:
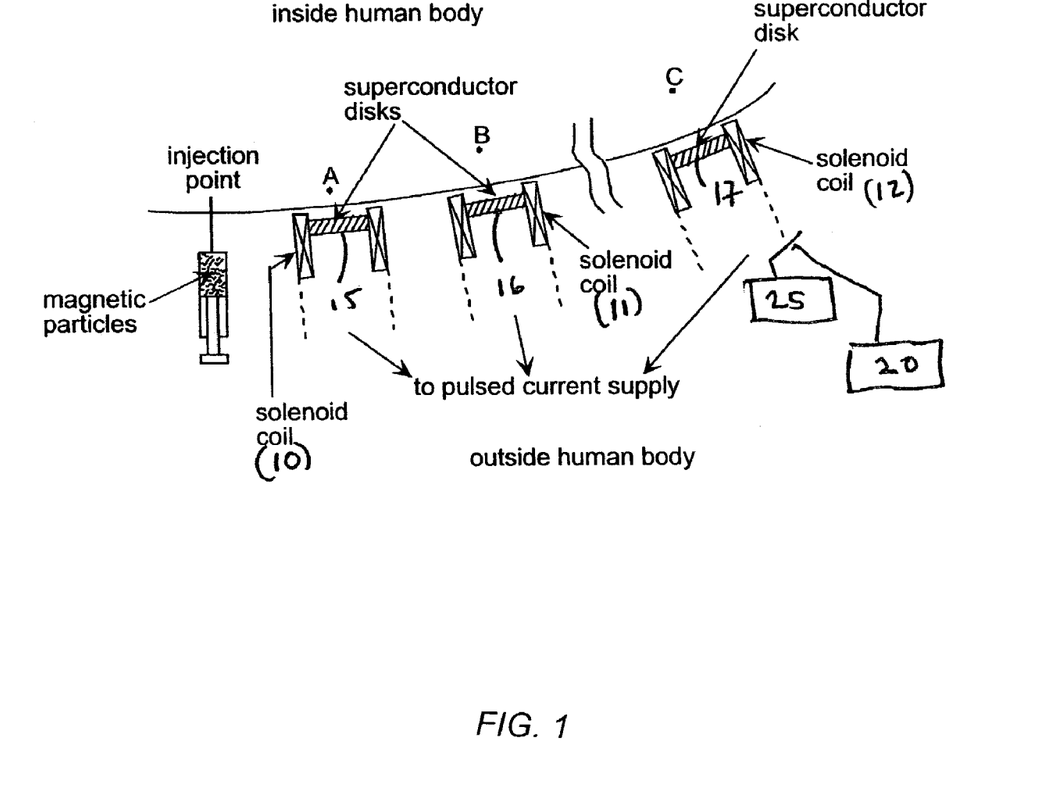
FIG. 1 is a schematic diagram of the system of the present invention.

Referring to FIG. 1, there is shown a schematic diagram of how magnetic material, such as particles or parts can be manipulated in human tissue. In order to hold the magnetic material in position A for a certain period of time to collect all the material coming in from an injection point, and then move the magnetic material to position B and hold it there for a certain period of time, and then repeating the same procedure until the material reach the desired position C in the tissue or the blood vessel, the system or apparatus of FIG. 1 can be used.

As shown in FIG. 1, two solenoid coils 10, 11 are located near position A and B, respectively. Inside each coil 10, 11 is a cylindrical high-Tc superconductor disk 15, 16, respectively. The solenoid coil 10, 11 is connected electrically to a current supply 20, which can generate either pulsed or DC current. The solenoid coils 10, 11 and the high-Tc superconductors 15, 16 are cooled in liquid nitrogen at 77 K.

Just before the injection of the magnetic material, such as for instance, particles, into the human tissue or blood vessel, a pulsed current is applied to the solenoid 10 near position A. After the pulsed current is gone, there remains a very large persistent current in the superconductor disk 15. This is the result of flux pinning, which is a unique property of type-II superconductors (high-Tc superconductor is type II). The consequence is that a very strong magnetic filed is trapped inside and around the superconductor disk 15. The superconductor disk 15 now becomes a strong permanent magnet. The advantage of using a trapped-field superconductor disk 15, instead of a normal permanent magnet, is that the superconductor can be de-magnetized by reversing the current flow in the solenoid 10.

After the superconductor disk 15 has been magnetized, the injection of the magnetic particles can begin. The magnetic particles will be attracted towards the superconductor disk 15 and eventually remained pinned near the surface of the superconductor disk 15. The magnetic particles will remain at the surface of the superconductor disk 15 as long as the persistent current is circulating in the superconductor 15. To move the magnetic particles from position A to position B, a pulsed current is first sent to the solenoid 11 near position B to trap magnetic field in the superconductor disk 15 in the coil. Then a second pulsed current, in the opposite direction of the original pulsed current, is sent to the solenoid coil 10 near position A. This second pulsed current will tend to demagnetize the superconductor disk 15 in the solenoid coil 10 near position A so that it can no longer hold the magnetic particles there. The magnetic particles will be attracted toward the superconductor disk near position B because it has been magnetized and a persistent current is flowing inside the superconductor disk 16. By placing the solenoid coil/superconductor disk combination (such as combination 12, 17 at position C) at strategic locations, the magnetic material, including particles, can be moved to the final destination and held there as long as it is needed. If it is desirable to retrieve the magnetic particles, the process can be reversed, all with the use of a standard control system 25 for introducing various pulsed currents to the solenoids and for changing directions of the current as needed.

An alternate method of de-magnetizing the superconductor disk or coil is to increase the temperature of the superconductor by using resistance heaters wrapped around the disk. By increasing the temperature of the superconductor to near or above the critical temperature (92 K for YBCO), the superconductor material will be de-magnetized, because the superconductor can no longer sustain a persistent current at temperatures above the critical temperature. The example given here is for moving magnetic particles in human tissues, including blood vessels is for illustration and is not to limit of the invention which also includes the use of magnetic particles for delivering drugs and therapy. Delivery of radioactive isotopes for cancer treatment and drugs for blood clots are two prominent examples. Moreover, the inventive method can also be used to move catheters with magnetic tips for drug delivery and therapy. In addition, the ability to modulate motion and reverse direction in the inventive method, apparatus and system enables application for nondestructive remote blood flow control. The invention is applicable to surgery and for prompt hemorrhage control in stroke victims. Furthermore, the inventive method and apparatus are not limited to medical applications, but applies to various industrial processes such as magnetic separations and magnetic conveyer systems (different types of magnetic separation and conveyer systems as found in Perry's Chemical Engineers' Handbook, McGraw-Hill Book Company, 6$^{th}$ edition, by R. H. Perry and D. W. Green, Section 21, pp. 33–41, 1984) the disclosure of which is incorporated by reference. This proposed method of propulsion and control is relevant to those applications.

The advantages of using a pulsed current, instead of a DC (constant current), are well known. The most important advantage of using a pulsed current is that less heat is generated in the solenoid coil, which translates into reduced cooling requirements, less bulky devices, and much higher magnetic fields. All are important for the present applications. Another advantage of using a pulsed current is that during the period while the current is changing, eddy currents are induced in the magnetic particles. The eddy currents in the magnetic particles may generate a repulsive force between the particles and the solenoid coil. Furthermore, the ability to rapidly switch the attractive force on the magnetic particles off and on can offer significant advantages over stationary or moving permanent magnets. One is the ability to synchronize the particle motion with the patient's heart beat. The inventive system is more flexible and can achieve better control than current devices using permanent magnets.

The superconductor can be either a cylindrical disk or a cylindrical ring or coil. The superconductor can also be a stack of rings (a cylindrical tube), or a stack of disks (a solid cylinder). The superconductor disk/ring can be BSCCO, YBCO, or other types of high-Tc superconductors, such as for example $SmBa_2Cu_3O_7$, $TlBa_2Ca_2Cu_3O_9$, $Tl_2Ba_2Ca_2Cu_3O_{10}$, $HgBa_2Ca_2Cu_3O_8$, and $MgB_2$.

Superconductors must be cooled to below the critical temperature thereof to sustain persistent currents and trapped fields. Liquid nitrogen cooling or a cryocooler is required to remove heat. The solenoid coils can be either a superconductor coil or a conventional copper coil. The former has to be cooled cryogenically with the superconductor disk and the latter can be cooled by air, water, or liquid nitrogen. If the copper solenoid coil is cooled by liquid nitrogen, then the system becomes simpler because both the superconductor disk and the copper coil can be submerged in liquid nitrogen in the same cryogenic container. This design has the added advantage of achieving very high pulsed current because the resistance of copper also decreases with decreasing temperature. If the targeted area is well inside the human body or head and a high magnetic field is required to propel and control the magnetic particles, the solenoid/superconductor is placed on either side of the body or head. For example, a pair of solenoid/superconductor system is placed on either side of the ears of a human head. Other possible arrangement of the coil/superconductor array are hereinafter disclosed. To trap larger fields (>1 Tesla), it is believed temperatures below 77 K are required.

As described previously, the inventive method of moving magnetic particles in human tissues and other systems depends on using pulsed current to magnetize (flux pinning) and de-magnetize (de-pinning) the superconductor disk or ring coil in the solenoid coil. The shape and duration of the pulsed current thus play a very important role in achieving the optimum conditions for effectively propelling the magnetic material (particles) to the desired location.

Magnetization and de-magnetization experiments were conducted for both a superconductor ring/coil system and a superconductor disk/coil system. The experimental apparatus is shown schematically in FIG. 2. A YBCO or other high temperature superconductor ring is placed inside a copper coil 35. The superconductor ring 30 has an outside diameter of 26.3 mm, a wall thickness of 8.2 mm, and a height of 8.0 mm. The copper coil 35 has a total number of turns of 100 and is made of copper wire with a diameter of 1.65 mm. The coil 35 has an outside diameter of 45.4 mm, an inside diameter of 28.9 mm, and a height of 44.7 mm. The top of the ring 30 is mounted just slightly below the top of the copper coil 35 so that a transparent non-magnetic container (not shown) can be placed directly on top of the superconductor ring. The copper coil 35 is electrically connected to a pulsed current supply. A hall probe 40 is placed at the center of the ring at a level just slightly above (1 mm) the top of the superconductor ring. The Hall probe 40 is connected to a Gaussmeter (not shown), which provides the reading of the magnetic field.

Figure 2:
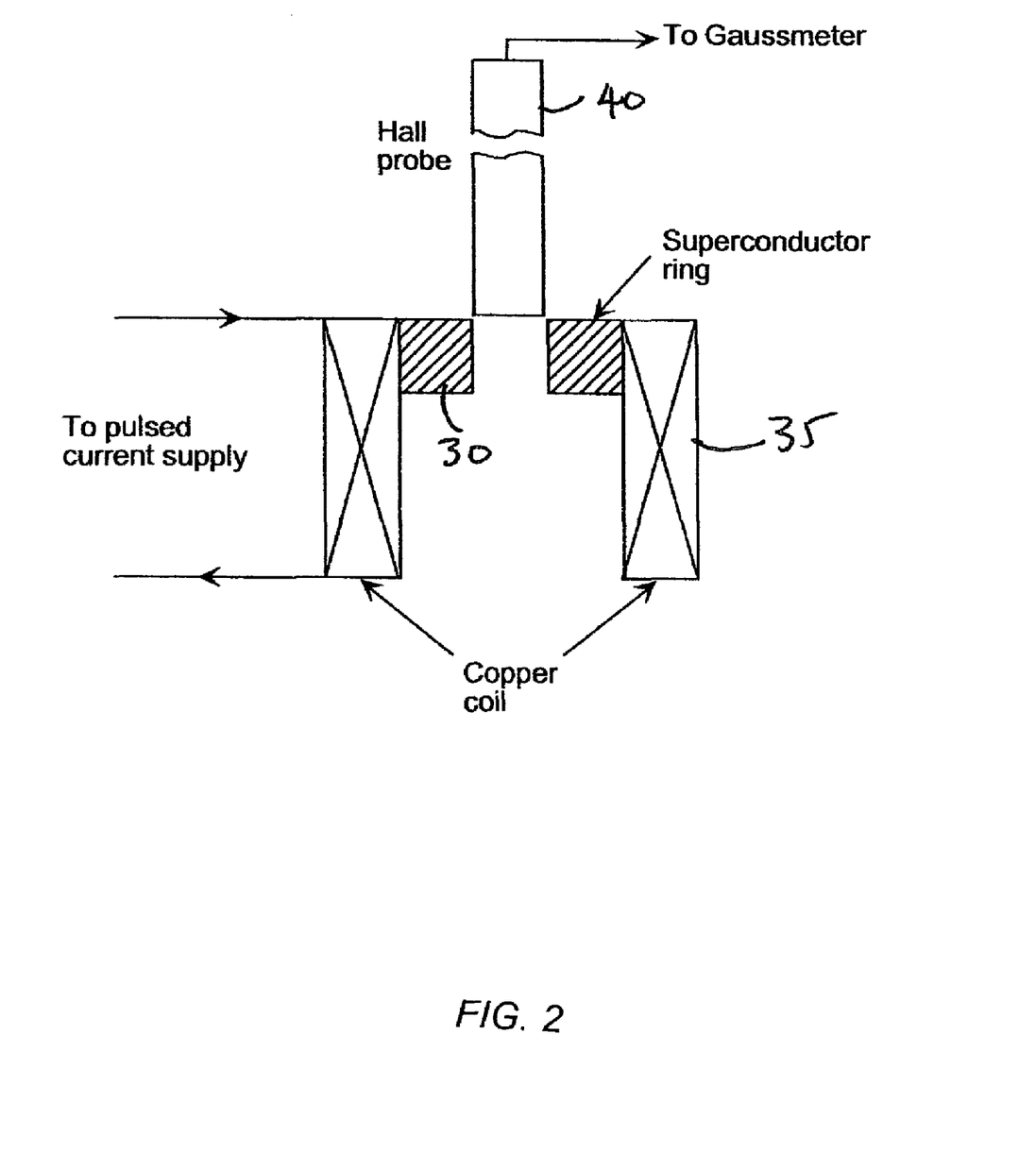
FIG. 2 is a graph of experimental apparatus for practicing the present invention.

When the copper coil/superconductor ring is cooled to liquid nitrogen temperature (77 K), a pulsed current is sent through the copper coil 35 to magnetize the superconductor ring 30. A typical current profile is shown in FIG. 3 for a superconductor disk, the current profile for a superconducting ring will be similar but not identical.

Figure 3:
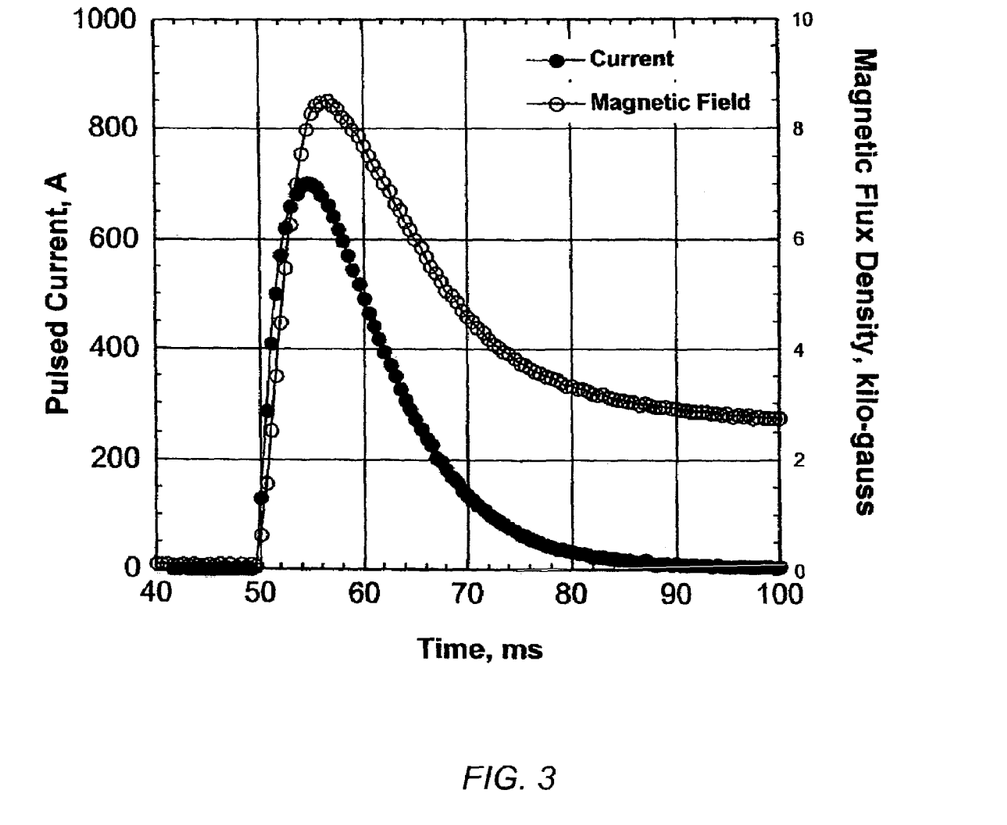
FIG. 3 is a graphical representation of the relationship between pulsed current in amperes and time in milliseconds for persistent currents and trapped magnetic fields.

FIG. 3 shows that the pulsed current of approximately 700 amperes, a trapped magnetic field is established which at its maximum is about 850 kilo-gauss and decays toward a steady state of 2.2 kilo-gauss.

To demonstrate that the trapped field can attract magnetic particles, the Hall probe 40 was removed from the test section to make room for the non-magnetic container. Ferromagnetic particles made of iron in fine powder form were placed inside the container. When the container was far away from the superconductor ring, the iron powder was spread over the entire area of the container randomly. As soon as the container was brought in and placed on top of the superconductor ring, the magnetic particles (powder) moved immediately towards the superconductor ring and formed a different and concentrated pattern, because the trapped field in the superconductor ring produced an attractive force between the magnetic particles and the superconductor ring.

Figure 4:
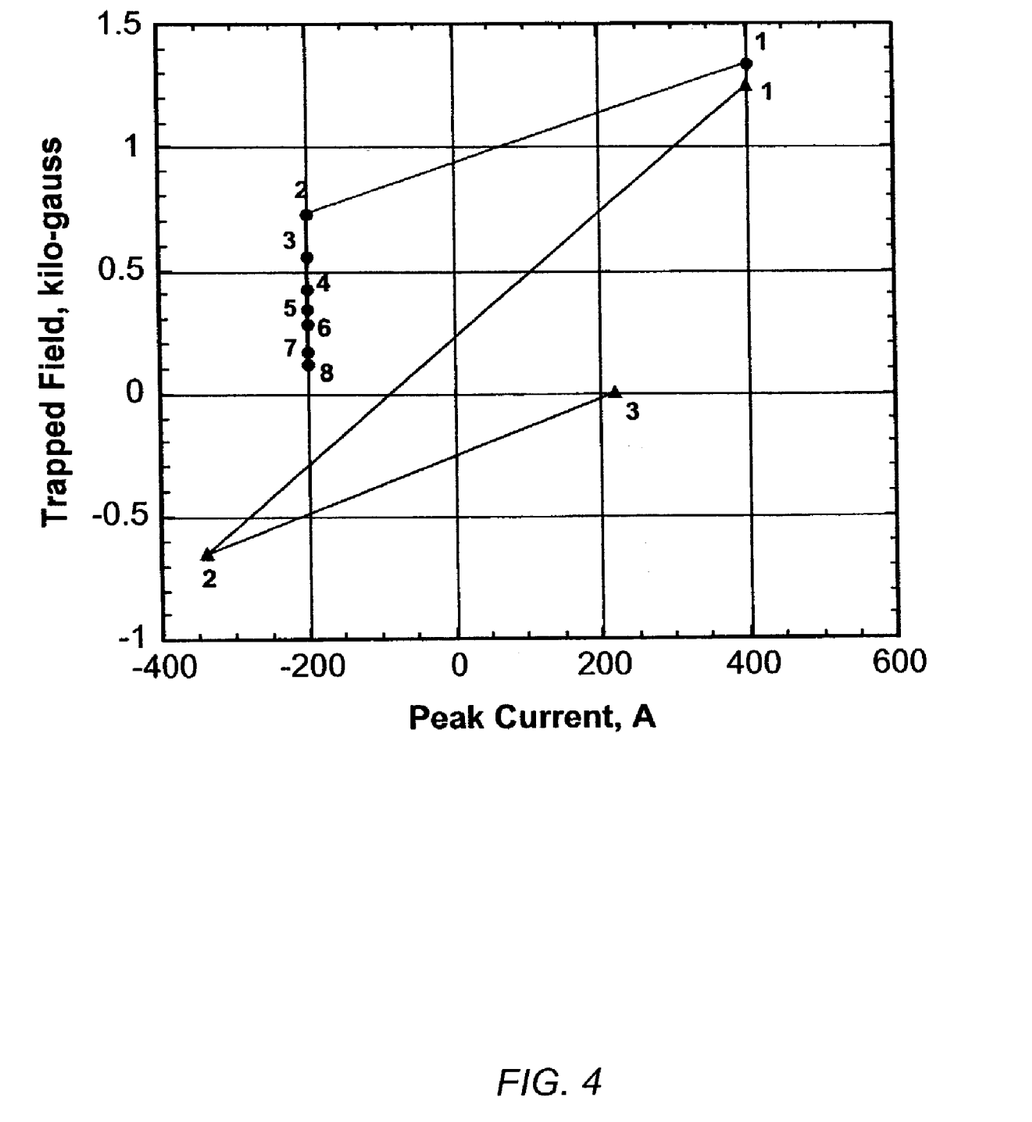
FIG. 4 is a graphical representation showing the relationship between trapped magnetic fields in kilo-gauss and peak currents in amperes for a superconducting ring and coil combination.

The magnetized superconductor disk/ring possesses the property of a permanent magnet and attracts magnetic particles, but also can be de-magnetized by reversing the direction of the pulsed current. FIG. 4 shows the result of the de-magnetization experiment. Starting with a trapped field of approximately 1.30 kilo-gauss, generated by a pulsed current with a peak amplitude of approximately 400 A, two different paths for de-magnetization are illustrated. The first path is indicated by the solid circles in FIG. 3. By reversing the direction of the pulsed current and using a peak current of −200 A, the trapped field is reduced to 0.1 kilo-gauss after seven pulses as shown in FIG. 9. The second path for de-magnetization is indicated by the solid triangles. By reversing the direction of the pulsed current and using a peak current of −340 A, the trapped field is reversed to −0.67 kilo-gauss. If the direction of the pulsed current is reversed again with a peak current of 200 A, the trapped field is returned to zero. There are other paths one can take to de-magnetize the superconductor ring. The objective is to illustrate that the superconductor ring/disk can be de-magnetized by reversing the pulsed current (with various amplitudes). This feature provides considerable flexibility for controlling the movement of magnetic particles.

A permanent magnet cannot be easily de-magnetized. Furthermore, the magnitude of the magnetic field generated by a permanent can not be changed either. The magnitude and direction of the trapped field in a superconductor disk/ring can be varied using pulsed current of various amplitudes and directions. In addition to flexibility and better control, a superconductor can trap a field much larger than that produced by permanent magnet. All this factors make the inventive pulsed-current superconductor system much more attractive than a system utilizing permanent magnets. Present superconducting solenoids use low-Tc superconductors, which require the use of liquid helium to cool the system to 4.2 K. A liquid helium system is more expensive and difficult to operate than a liquid nitrogen system. Furthermore, a low-Tc based superconducting solenoid cannot be easily magnetized and de-magnetized as can the inventive solenoid/superconductor disk system. Quenching the superconducting magnet is another limitation of the low-Tc based superconducting system. Therefore, the low-Tc superconductor based superconducting solenoid system cannot provide the flexibility offered by the inventive system.

Both disks and rings were used in the experiments. Two almost identical superconductor rings were stacked together and placed inside a copper coil. The top of the two rings were mounted just slightly below the top of the coil. The disk/coil system was placed in the open foam dewar. The superconductor disk had a diameter of about 19.4 mm and the height was equal to 3.7 mm. The total height of the two disks was equal to 7.4 mm. The copper coil had 100 turns with an inside diameter of 20.6 mm (slightly larger than the diameter of the superconductor disks). The outside diameter of the coil was 35.4 mm. The coil had an axial length of 33.3 mm.

Figure 5:
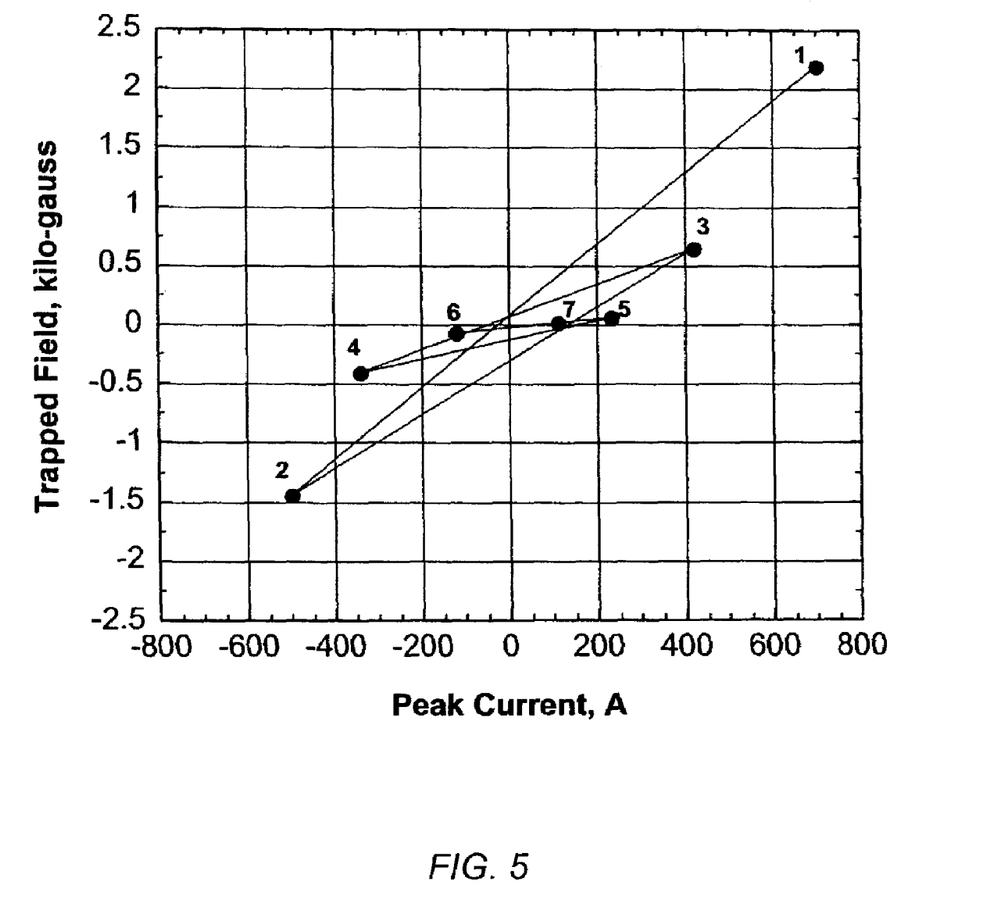
FIG. 5 is a graphical representation of the relationship between a trapped field in kilo-gauss and peak current in amperes for a disc/coil apparatus.

The result of a de-magnetization test is shown in FIG. 5. The numbers indicate the sequence of the test. First, the superconductor disks were magnetized to 2.2 kilo-gauss (data point 1) by using the a pulsed current with a peak amplitude of 700 A. Data points 2 to 7 indicate the path of the de-magnetization process. In this particular de-magnetization test, we alternated the pulsed current direction in decreasing peak amplitude. The superconductor disks were almost completely de-magnetized with 6 pulses (data point 7). As mentioned previously, de-magnetization can follow many different paths and the result in FIG. 5 is just one of them.

Figure 6:
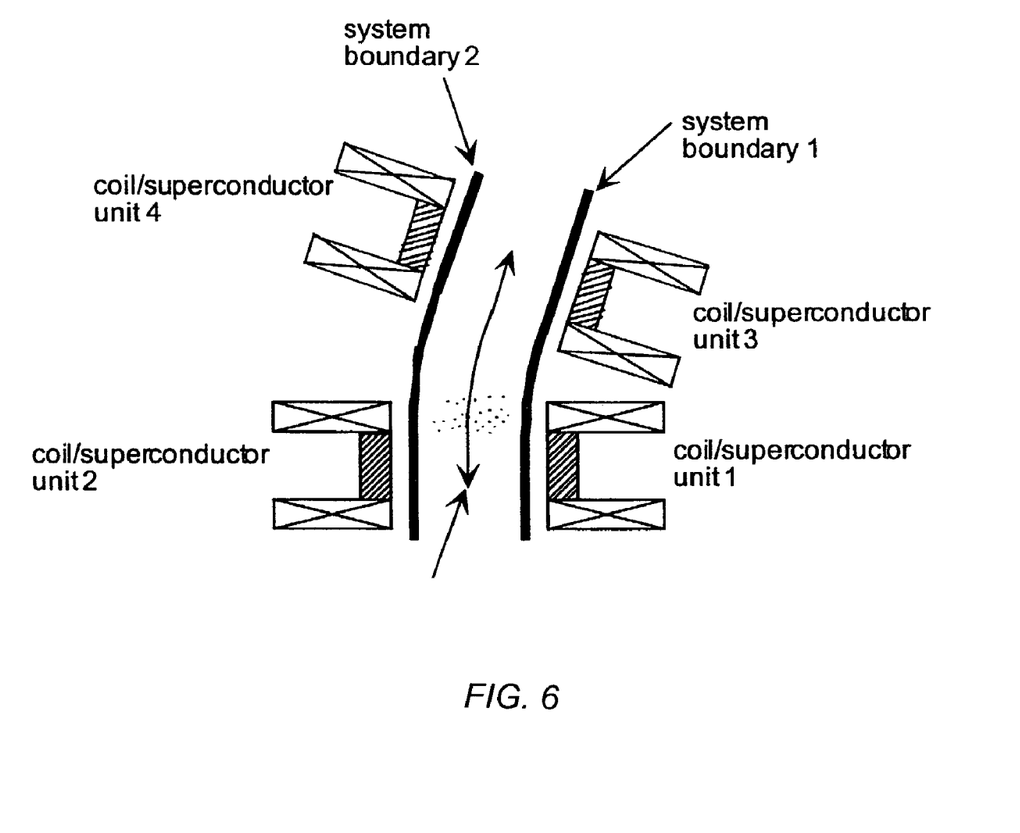
FIG. 6 is a schematic representation of a one-dimensional arrangement of coil/superconductor units along the path of particle motion.
Figure 7:
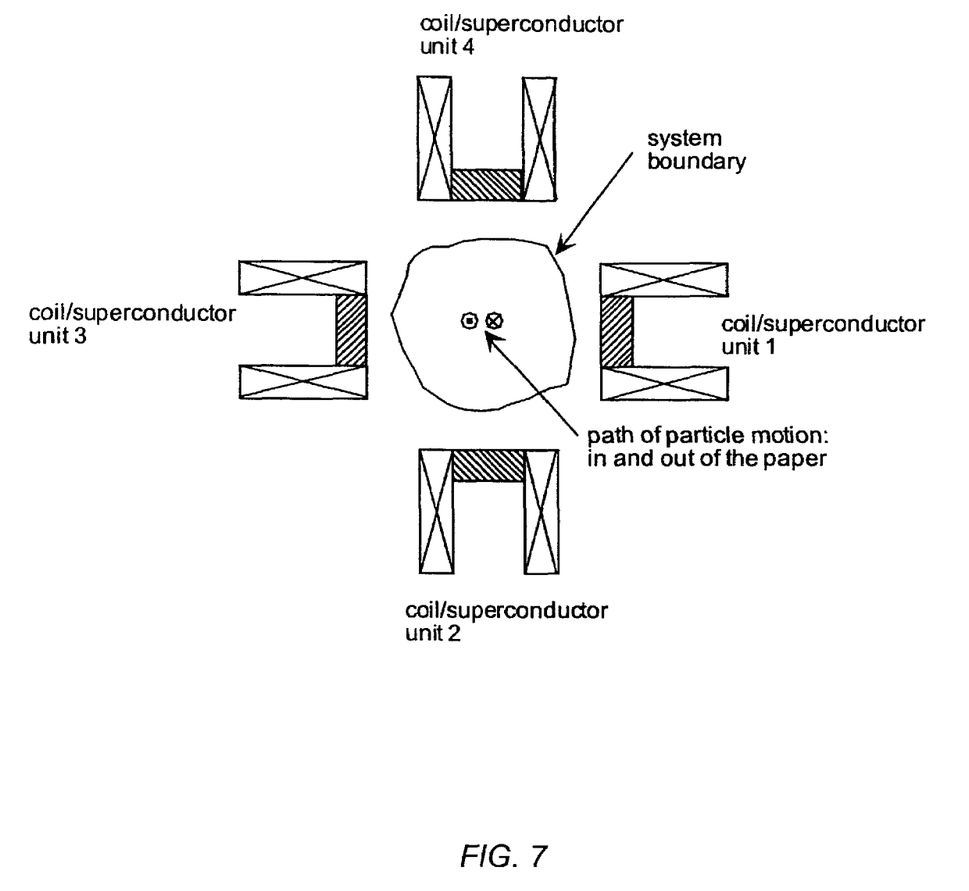
FIG. 7 is a two-dimensional array arrangement of coil/superconductor units at a given location or elevation along the path of particle motion.

The configuration shown in FIG. 1 is just one particular arrangement of the solenoid coil/superconductor units. Other array arrangements are also possible and may be more effective (depending on specific applications). For example, instead of placing the coil/superconductor unit along one side of the physical boundary of the system, one coil/superconductor unit can be placed on either side of the system boundaries as shown in FIG. 6. This arrangement can provide stronger magnetic field and field gradient (hence the forces) than that shown in FIG. 1. A two-dimensional array of coil/superconductor unit can also be employed as shown in FIG. 7. This further increases the magnetic forces for moving the magnetic particles and provides better control. If space is available, one can even use a three-dimensional array similar to that employed by the Magnetic Stereotaxis System (MSS), as described by D. C. Meeker, E. H. Maslen, R. C. Ritter and F. M. Creighton, Optimal Realization of Arbitrary Forces in a Magnetic Stereotaxis Systems, IEEE Trans. on Magnetics, Vol. 32, No. 2, March 1996, PP. 320–328, the disclosure of which is incorporated by reference. The MSS employs six superconducting coils, with two coils located at the front and the back of the head, two coils on either side of the ears, one coil on top of the head, and one coil below the jaw. The MSS uses low-temperature superconductors and requires liquid helium cooling. In addition, the current ramp rate is limited because of quenching problems associated with low-temperature superconductors.

The shape of the pulsed current is an important factor in controlling the magnetic material motion. In addition to controlling the amplitude of the current pulse, we can control the duration, the rise time, and the shape of the current pulse. In FIG. 3, the duration of the current pulse is less than 100 mili-seconds (ms). The rise time (the slope of the current profile) is about 100,000 Amperes/second. This is a very fast process. The duration and rise time of the current pulse, if necessary, can be either increased or decreased to satisfy the need of the specific application. The shape of the pulse can also be changed, as is known in the art. For example, instead of the sinusoidal pulse shape shown in FIG. 3, a square shaped pulse can be generated. Other pulse shapes can easily be employed to meet the requirements of the specific applications. All these factors, the amplitude, the rise time, the duration, and the shape of the current pulse will affect the magnetic field trapped by the superconductor disk or ring. Therefore, these factors will also affect the magnetic forces exerted on the magnetic materials (particles).

While particular embodiments of the present invention have been shown and described, it will be appreciated by those skilled in the art that changes, modifications and improvements may be made, for example in the processing of the materials or in the electrode and/or cell design without departing from the true spirit and scope of the invention.

The embodiments of the invention in which an exclusive property or privilege is claimed are defined as follows:

1. A method of controlling movement of magnetic material, comprising providing at least first and second high temperature superconductors at spaced locations, magnetizing at least one of said high temperature superconductors to establish a first magnetic field, magnetizing at least one other of said high temperature superconductors to establish a second magnetic field, and demagnetizing at least one of said high temperature superconductors to reduce the first magnetic field substantially to zero, whereby magnetic material near said first magnetic field will be attracted thereto during the presence thereof and when said first magnetic field is reduced substantially to zero the magnetic material will be attracted to said second magnetic field, thereby causing movement of magnetic material toward and away from said first and second magnetic fields.

2. The method of claim 1, wherein the high temperature superconductor has a general formula of $YBa_2Cu_3O_7$.

3. The method of claim 1, wherein the high temperature superconductor has a general formula of $Bi_2Sr_2Ca_2Cu_3O_{10}$ or $Bi_2Sr_2Ca_1Cu_2O_8$.

4. The method of claim 1, wherein the high temperature superconductor has a general formula of one or more of $SmBa_2Cu_3O_7$, $TlBa_2Ca_2Cu_3O_9$, $Tl_2Ba_2Ca_2Cu_3O_{10}$, $HgBa_2Ca_2Cu_3O_8$, and $MgB_2$.

5. The method of claim 1, wherein the magnetic field is a trapped field.

6. The method of claim 1, wherein the magnetic material is a particulate.

7. The method of claim 1, wherein the magnetic material is introduced into a warm blooded animal.

8. The method of claim 1, wherein the magnetic material is injected into a warm blooded animal.

9. The method of claim 1, wherein high temperature superconductors are positioned to define a predetermined path for moving magnetic material therealong.

10. A method of controlling movement of magnetic material, comprising providing at least first and second high temperature superconductors at spaced locations, introducing a persistent current in at least one of said high temperature superconductors to establish a first magnetic field, introducing a persistent current in at least one other of said high temperature superconductors to establish a second magnetic field, and demagnetizing at least one of said high temperature superconductors to reduce the first magnetic field substantially to zero, whereby magnetic material near said first magnetic field will be attracted thereto during the presence thereof and when said first magnetic field is reduced substantially to zero then the magnetic material will be attracted to said second magnetic field, thereby causing movement of magnetic material toward and away from said first and second magnetic fields.

11. The method of claim 10, wherein the persistent currents are introduced by locating a pulsed current near the high temperature superconductors.

12. The method of claim 10, wherein the pulsed, currents are applied to solenoids adjacent the superconductors.

13. The method of claim 12, wherein the demagnetization is accomplished by reversing the direction of the pulsed current.

14. The method of claim 10, wherein the demagnetization is accomplished by heating the superconductor beyond its critical temperature.

15. A system of controlling movement of magnetic material, comprising at least first and second high temperature superconductors at spaced locations, a plurality of solenoids associated with said superconductors to induce a persistent currents in preselected high temperature superconductors establishing a plurality of magnetic fields in response to pulsed currents introduced to one or more of said solenoids, and control mechanism in communication with said solenoids and/or said high temperature superconductors to demagnetize selected ones of said high temperature superconductors to reduce the magnetic fields substantially to zero, whereby magnetic material is moved between magnetic fields by establishing the presence thereof and thereafter reducing magnetic fields substantially to zero and establishing magnetic fields in other superconductors arranged in a predetermined configuration.

16. The system of claim 15, wherein the superconductor is one or more of the general formula $YBa_2Cu_3O_7$ or $Bi_2Sr_2Ca_2Cu_3O_{10}$ or $Bi_2Sr_2Ca_1Cu_2O_8$.

17. The system of claim 16, wherein the magnetic fields are trapped fields from persistent currents in said superconductors.

18. The system of claim 17, wherein magnetic fields are reduced substantially to zero by reversing the direction of the pulsed currents introduced into selected ones of said solenoids.

19. The system of claim 17, wherein magnetic fields are reduced substantially to zero by heating selected ones of said superconductors to temperatures higher than the critical temperature thereof.

20. The system of claim 17, wherein said superconductors are disks or rings.

21. The system of claim 17, wherein liquid nitrogen cooling mechanism is provided for said solenoids and said superconductors.

22. The system of claim 17, wherein said solenoids include coils of copper or a high-temperature superconductor.

23. The system of claim 17, wherein the control mechanism varies the shape, amplitude, rise time and duration of the pulsed currents.

24. The system of claim 15, wherein superconductors are arranged on opposite sides of the magnetic material.

25. The system of claim 24, wherein superconductors are arranged in a three dimensional pattern around the magnetic material.

* * * * *